United States Patent
Hebeisen et al.

(10) Patent No.: US 8,088,920 B2
(45) Date of Patent: Jan. 3, 2012

(54) 3-TRIFLUOROMETHYL-PYRAZINE-2-CARBOXYLIC ACID AMIDE DERIVATIVES AS HDL-CHOLESTEROL RAISING AGENTS

(75) Inventors: Paul Hebeisen, Basel (CH); Constantinos G. Panousis, Lyndhurst, NJ (US); Stephan Roever, Inzlingen (DE); Matthew Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 337 days.

(21) Appl. No.: 12/404,365

(22) Filed: Mar. 16, 2009

(65) Prior Publication Data

US 2009/0247550 A1    Oct. 1, 2009

(30) Foreign Application Priority Data

Mar. 31, 2008 (EP) .................................. 08153802

(51) Int. Cl.
*A81K 31/497*   (2006.01)
*C07D 241/00*   (2006.01)

(52) U.S. Cl. ..................................... 544/336; 514/252.1
(58) Field of Classification Search .................. 544/336; 514/252.1

See application file for complete search history.

(56) References Cited

U.S. PATENT DOCUMENTS

| | | | |
|---|---|---|---|
| 4,293,552 | A | 10/1981 | Miesel |
| 7,229,999 | B2 | 6/2007 | Hebeisen et al. |
| 2006/0229326 | A1 | 10/2006 | Hebeisen et al. |
| 2007/0293509 | A1 | 12/2007 | Hebeisen et al. |
| 2008/0070931 | A1 | 3/2008 | Hebeisen et al. |
| 2008/0085905 | A1 | 4/2008 | Dietz et al. |
| 2008/0085906 | A1 * | 4/2008 | Andjelkovic et al. .... 514/255.06 |

FOREIGN PATENT DOCUMENTS

| | | |
|---|---|---|
| WO | WO 2006/106054 | 10/2006 |
| WO | WO 2007/147746 | 12/2007 |
| WO | WO 2008/031734 | 3/2008 |
| WO | WO 2008/040651 | 4/2008 |
| WO | WO 2008/040649 | 10/2008 |

OTHER PUBLICATIONS

Shinkai, H: *MiniReveiws in Medicinal Chemistry*, (2002) 2:3 271-273 XP009113837.

* cited by examiner

*Primary Examiner* — Rei-tsang Shiao
(74) *Attorney, Agent, or Firm* — George W. Johnston; Patricia S. Rocha-Tramaloni; Gene J. Yao

(57) ABSTRACT

The present invention relates to pyrazine derivatives of the formula

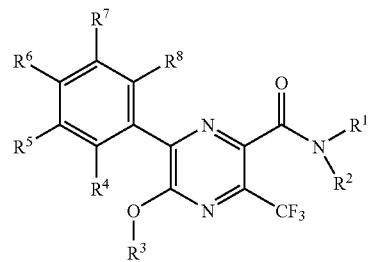

I and pharmaceutically acceptable salts thereof, wherein $R^1$ to $R^8$ are as defined in the description and claims for use as HDL-cholesterol raising agents in the treatment and/or prophylaxis of diseases or disorders that can be treated with such agents such as dyslipidemia.

20 Claims, No Drawings

3-TRIFLUOROMETHYL-PYRAZINE-2-CARBOXYLIC ACID AMIDE DERIVATIVES AS HDL-CHOLESTEROL RAISING AGENTS

PRIORITY TO RELATED APPLICATION(S)

This application claims the benefit of European Patent Application No. 08153802.7, filed Mar. 31, 2008, which is hereby incorporated by reference in its entirety.

BACKGROUND OF THE INVENTION

The present invention relates to 3-trifluoromethyl-pyrazine-2-carboxylic acid amide derivatives, their manufacture, pharmaceutical compositions containing them and their use as HDL-cholesterol raising agents. The compounds of the present invention are especially useful for the treatment of dyslipidemia.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, bypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, HDL-cholesterol raising agents may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

Object of the present invention is therefore to provide compounds which are potent HDL-cholesterol raising agents. It has been found that compounds of formula I of the present invention are useful for the treatment and/or prophylaxis of diseases which can be treated with HDL-cholesterol raising agents, i.e. compounds of formula I are especially useful for the treatment and/or prevention of dyslipidemia.

SUMMARY OF THE INVENTION

The present invention relates to the compounds of formula I:

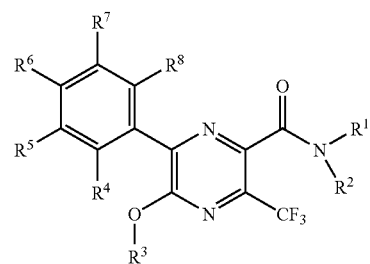

and pharmaceutically acceptable salts thereof, wherein:
$R^1$ is selected from the group consisting of:
(1) cycloalkyl, which is unsubstituted or substituted by hydroxy or lower hydroxyalkyl, and
(2) —$CH_2$—$CR^9R^{10}$-cycloalkyl, wherein $R^9$ is hydrogen or lower alkyl, and $R^{10}$ is hydrogen or hydroxy;
$R^2$ is hydrogen;
$R^3$ is selected from the group consisting of:
(1) lower cycloalkylalkyl,
(2) lower alkoxyalkyl,
(3) lower halogenalkyl,
(4) lower heteroarylalkyl, wherein the heteroaryl group is unsubstituted or substituted once or twice by lower alkyl, and
(5) phenyl, which is unsubstituted or substituted once or twice by halogen;
$R^4$ and $R^8$ independently from each other are hydrogen or halogen;
$R^5$, $R^6$ and $R^7$ independently from each other are selected from the group consisting of:
(1) hydrogen,
(2) lower alkyl,
(3) lower alkoxy,
(4) halogen,
(5) lower halogenalkyl,
(6) lower halogenalkoxy,
(7) lower alkylsulfonylamino, and
(8) cyano.

The compounds of formula I are HDL-cholesterol raising agents and are useful in the treatment and/or prophylaxis of diseases or disorders that can be treated with such agents such as dyslipidemia.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atom(s). In preferred embodiments a "lower" group has one to four carbon atom(s).

The term "alkyl", alone or in combination with other groups, refers to a branched or straight-chain monovalent saturated aliphatic hydrocarbon radical of one to twenty carbon atoms. In preferred embodiments the akyl has one to sixteen carbon atoms, and more preferably one to ten carbon atoms.

The term "lower alkyl" or "$C_{1-7}$-alkyl", alone or in combination with other groups, refers to a branched or straight-chain monovalent alkyl radical of one to seven carbon atoms. In preferred embodiments the lower akyl has one to four carbon atoms. This term is exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups include methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups include —$CH_2$—O—$CH_3$, —$CH_2$—$CH_2$—O—$CH_3$, —$CH_2$—O—$CH_2$—$CH_3$ and the groups specifically exemplified herein. Most preferably, lower alkoxyalkyl is methoxyethyl.

The term "lower hydroxyalkyl" or "hydroxy-$C_{1-7}$-alkyl" refers to a lower alkyl group as defined above wherein at least one of the hydrogen atoms of the lower alkyl group is replaced by a hydroxy group. Preferred are $C_{3-7}$-hydroxyalkyl groups. Examples of lower hydroxyalkyl groups include 2-hydroxybutyl, 3-hydroxy-2,2-dimethylpropyl and the groups specifically exemplified therein.

The term "halogen" refers to fluoro, chloro, bromo and iodo. Preferred "halogen" groups are fluoro or chloro.

Unless otherwise indicated, the term "hydrogen" or "hydro" refers to the moiety of a hydrogen atom (—H) and not $H_2$.

The term "lower halogenalkyl" or "halogen-$C_{1-7}$-alkyl" refers to a lower alkyl group which is mono- or multiply substituted with halogen. In preferred embodiments the halogen of a lower halogenalkyl is fluoro or chloro, most preferably fluoro. Examples of lower halogenalkyl groups include —$CF_3$, —$CHF_2$, —$CH_2Cl$, —$CH_2CF_3$, —$CH(CF_3)_2$, —$CF_2$—$CF_3$ and the groups specifically exemplified herein.

The term "lower halogenalkoxy" or "halogen-$C_{1-7}$-alkoxy" refers to a lower alkoxy group as defined above wherein at least one of the hydrogen atoms of the lower alkoxy group is replaced by a halogen atom. In preferred embodiments, the halogen of a lower halogenalkoxy group is fluoro or chloro, and most preferably fluoro. Among the preferred lower halogenalkoxy groups are trifluoromethoxy, difluoromethoxy, fluormethoxy and chloromethoxy, with trifluoromethoxy being especially preferred.

The term "cycloalkyl" or "$C_{3-7}$-cycloalkyl" refers to a monovalent carbocyclic radical of three to seven carbon atoms. In preferred embodiments the cycloalkyl has three to five carbon atoms. This term is exemplified by radicals such as cyclopropyl, cyclobutyl, cyclopentyl, cyclohexyl and cycloheptyl, with cyclopropyl being especially preferred.

The term "lower cycloalkylalkyl" or "$C_{3-7}$-cycloalkyl-$C_{1-7}$-alkyl" refers to a lower alkyl group as defined above which is mono- or multiply substituted with a cycloalkyl group as defined above. Examples of lower cycloalkylalkyl groups include —$CH_2$-cyclopropyl, —$CH_2$—$CH_2$-cyclopropyl, —$CH_2$-cyclopentyl and the groups specifically exemplified herein.

The term "heteroaryl" refers to an aromatic 5- or 6-membered ring which comprises one, two or three heteroatoms selected from the group consisting of nitrogen, oxygen and sulphur. Examples of heteroaryl groups include furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, and pyrrolyl. The heteroaryl group can optionally be mono- or disubstituted by lower alkyl. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrimidinyl, imidazolyl, triazolyl, and thiazolyl which groups can optionally be mono- or disubstituted by lower alkyl. Especially preferred are 3-methylisoxazolyl, 5-methylisoxazolyl, pyridyl, 3-methylpyridyl, pyrimidinyl, 1-methylimidazolyl, 2-methyl[1,2,4]triazolyl and 4-methylthiazolyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "lower alkylsulfonyl" or "$C_{1-7}$-alkylsulfonyl" refers to the group R'—$SO_2$—, wherein R' is lower alkyl. Examples of lower alkylsulfonyl groups include methanesulfonyl and ethanesulfonyl.

The term "lower alkylsulfonylamino" or "$C_{1-7}$-alkylsulfonylamino" refers to the group R'—$SO_2$—NH—, wherein R' is lower alkyl. A preferred lower alkylsulfonylamino group is methanesulfonylamino.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

Unless otherwise indicated, in reference to a particular group or molecule, the term "substituted" refers to the fact that at least one of the hydrogen atoms of that group or molecule is replaced by some other substituent.

The term "MS" refers to mass spectrometry.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt of any such compound).

In detail, the present invention relates to the compounds of formula I:

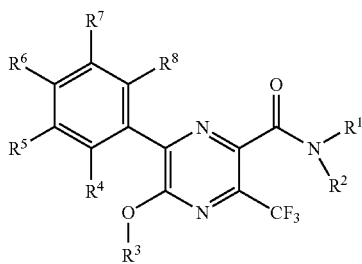

I and pharmaceutically acceptable salts thereof, wherein:
$R^1$ is selected from the group consisting of:
  (1) cycloalkyl, which is unsubstituted or substituted by hydroxy or lower hydroxyalkyl, and
  (2) —$CH_2$—$CR^9R^{10}$-cycloalkyl, wherein $R^9$ is hydrogen or lower alkyl, and $R^{10}$ is hydrogen or hydroxy;
$R^2$ is hydrogen;
$R^3$ is selected from the group consisting of:
  (1) lower cycloalkylalkyl,
  (2) lower alkoxyalkyl,
  (3) lower halogenalkyl,
  (4) lower heteroarylalkyl, wherein the heteroaryl group is unsubstituted or substituted once or twice by lower alkyl, and
  (5) phenyl, which is unsubstituted or substituted once or twice by halogen;
$R^4$ and $R^8$ independently from each other are hydrogen or halogen;
$R^5$, $R^6$ and $R^7$ independently from each other are selected from the group consisting of:
  (1) hydrogen,
  (2) lower alkyl,
  (3) lower alkoxy,
  (4) halogen,
  (5) lower halogenalkyl,
  (6) lower halogenalkoxy,
  (7) lower alkylsulfonylamino, and
  (8) cyano.

Preferred compounds of formula I according to the invention are those, wherein $R^3$ is selected from the group consisting of lower cycloalkylalkyl, lower halogenalkyl and lower heteroarylalkyl, wherein the heteroaryl group is unsubstituted or mono- or di-substituted by lower alkyl.

More preferred are compounds of formula I, wherein $R^3$ is lower halogenalkyl, with those compounds of formula I, wherein $R^3$ is 2,2,2-trifluoroethyl, being especially preferred.

Furthermore, compounds of formula I are preferred, wherein $R^3$ is lower cycloalkylalkyl, with those compounds of formula I being especially preferred, wherein $R^3$ is cyclopropylmethyl.

Also preferred are compounds of formula I, wherein $R^3$ is lower heteroarylalkyl, wherein the heteroaryl group is unsubstituted or mono- or di-substituted by lower alkyl, with those compounds of formula I, wherein $R^3$ is pyridylmethyl, being especially preferred.

Also preferred are compounds of formula I of the present invention, wherein $R^3$ is phenyl.

Furthermore, compounds of formula I according to the invention are preferred, wherein $R^1$ is cycloalkyl substituted by hydroxy, with those compounds, wherein $R^1$ is cyclohexyl substituted by hydroxy, being especially preferred.

Another group of preferred compounds of formula I according to the present invention are those, wherein $R^1$ is —$CH_2$—$CR^9R^{10}$-cycloalkyl and wherein $R^9$ is methyl and $R^{10}$ is hydroxy, with those compounds of formula I, wherein $R^1$ is —$CH_2$—$CR^9R^{10}$-cyclopropyl and wherein $R^9$ is methyl and $R^{10}$ is hydroxy, being more preferred.

Also preferred are compounds of formula I according to the invention, wherein at least one of $R^5$, $R^6$ and $R^7$ is selected from the group consisting of lower alkyl, halogen, lower halogenalkyl, lower halogenalkoxy, lower alkylsulfonylamino and cyano.

Furthermore, compounds of formula I are preferred, wherein at least one of $R^5$, $R^6$ and $R^7$ is selected from halogen or lower alkylsulfonylamino, with those compounds of formula I, wherein $R^6$ is halogen or lower alkylsulfonylamino and $R^6$ and $R^7$ are hydrogen, being more preferred. Especially preferred are compounds of formula I, wherein $R^6$ is chloro.

Also preferred are compounds of formula I according to the invention, wherein $R^5$ and $R^6$ are halogen and $R^7$ is hydrogen. Especially preferred are compounds of formula I, wherein $R^5$ and $R^6$ are chloro.

Preferred compounds of formula I according to the invention are selected from the group consisting of:
6-(4-chloro-phenyl)-5-(2,2,2-trifluoro-ethoxy)-3-trifluoromethyl-pyrazine-2-carboxylic acid (2-cyclopropyl-2-hydroxy-propyl)-amide,
6-(4-chloro-phenyl)-5-cyclopropylmethoxy-3-trifluoromethyl-pyrazine-2-carboxylic acid ((1R,2R)-2-hydroxy-cyclohexyl)-amide,
6-(4-chloro-phenyl)-5-cyclopropylmethoxy-3-trifluoromethyl-pyrazine-2-carboxylic acid (2-cyclopropyl-2-hydroxy-propyl)-amide,
6-(3-chloro-phenyl)-5-(2,2,2-trifluoro-ethoxy)-3-trifluoromethyl-pyrazine-2-carboxylic acid ((1R,2R)-2-hydroxy-cyclohexyl)-amide,
6-(3-chloro-phenyl)-5-(2,2,2-trifluoro-ethoxy)-3-trifluoromethyl-pyrazine-2-carboxylic acid (2-cyclopropyl-2-hydroxy-propyl)-amide,
6-(3-chloro-phenyl)-5-cyclopropylmethoxy-3-trifluoromethyl-pyrazine-2-carboxylic acid ((1R,2R)-2-hydroxy-cyclohexyl)-amide,
6-(3-chloro-phenyl)-5-cyclopropylmethoxy-3-trifluoromethyl-pyrazine-2-carboxylic acid (2-cyclopropyl-2-hydroxy-propyl)-amide,
6-(3-chloro-phenyl)-5-phenoxy-3-trifluoromethyl-pyrazine-2-carboxylic acid ((1R,2R)-2-hydroxy-cyclohexyl)-amide,
6-(3-chloro-phenyl)-5-phenoxy-3-trifluoromethyl-pyrazine-2-carboxylic acid (2-cyclopropyl-2-hydroxy-propyl)-amide, 6-(3-chloro-phenyl)-5-(pyridin-2-ylmethoxy)-3-trifluoromethyl-pyrazine-2-carboxylic acid ((1R,2R)-2-hydroxy-cyclohexyl)-amide, 6-(3-chloro-phenyl)-5-(pyridin-2-ylmethoxy)-3-trifluoromethyl-pyrazine-2-carboxylic acid (2-cyclopropyl-2-hydroxy-propyl)-amide, 6-(3,4-dichloro-phenyl)-5-(2,2,2-trifluoro-ethoxy)-3-trifluoromethyl-pyrazine-2-carboxylic acid ((1R,2R)-2-hydroxy-cyclohexyl)-amide, 6-(3,4-dichloro-phenyl)-5-(2,2,2-trifluoro-ethoxy)-3-trifluoromethyl-pyrazine-2-carboxylic acid (2-cyclopropyl-2-hydroxy-propyl)-amide, 6-(3,4-dichloro-phenyl)-5-cyclopropylmethoxy-3-trifluoromethyl-pyrazine-2-carboxylic acid ((1R,2R)-2-hydroxy-cyclohexyl)-amide, 6-(3,4-dichloro-phenyl)-5-cyclopropylmethoxy-3-trifluoromethyl-pyrazine-2-carboxylic acid (2-cyclopropyl-2-hydroxy-propyl)-amide, 6-(3,4-dichloro-phenyl)-5-phenoxy-3-trifluoromethyl-pyrazine-2-carboxylic acid ((1R,2R)-2-hydroxy-cyclohexyl)-amide, 6-(3,4-dichloro-phenyl)-5-phenoxy-3-trifluoromethyl-pyrazine-2-carboxylic acid (2-cyclopropyl-2-hydroxy-propyl)-amide, 6-(3,4-dichloro-phenyl)-5-(pyridin-2-ylmethoxy)-3-trifluoromethyl-pyrazine-2-carboxylic acid ((1R,2R)-2-hydroxy-cyclohexyl)-amide, 6-(3,4-dichloro-phenyl)-5-(pyridin-2-ylmethoxy)-3-trifluoromethyl-pyrazine-2-carboxylic acid (2-cyclopropyl-2-hydroxy-propyl)-amide, 6-(4-methanesulfonylamino-phenyl)-5-(2,2,2-trifluoro-ethoxy)-3-trifluoromethyl-pyrazine-2-carboxylic acid ((1R,2R)-2-hydroxy-cyclohexyl)-amide, 6-(4-methanesulfonylamino-phenyl)-5-(2,2,2-trifluoro-ethoxy)-3-trifluoromethyl-pyrazine-2-carboxylic acid (2-cyclopropyl-2-hydroxy-propyl)-amide, 6-(4-methanesulfonylamino-phenyl)-5-cyclopropylmethoxy-3-trifluoromethyl-pyrazine-2-carboxylic acid ((1R,2R)-2-hydroxy-cyclohexyl)-amide, 6-(4-methanesulfonylamino-phenyl)-5-cyclopropylmethoxy-3-trifluoromethyl-pyrazine-2-carboxylic acid (2-cyclopropyl-2-hydroxy-propyl)-amide, 6-(4-methanesulfonylamino-phenyl)-5-phenoxy-3-trifluoromethyl-pyrazine-2-carboxylic acid ((1R,2R)-2-hydroxy-cyclohexyl)-amide, 6-(4-methanesulfonylamino-phenyl)-5-phenoxy-3-trifluoromethyl-pyrazine-2-carboxylic acid (2-cyclopropyl-2-hydroxy-propyl)-amide, 6-(4-methanesulfonylamino-phenyl)-5-(pyridin-2-ylmethoxy)-3-trifluoromethyl-pyrazine-2-carboxylic acid ((1R,2R)-2-hydroxy-cyclohexyl)-amide, 6-(4-methanesulfonylamino-phenyl)-5-(pyridin-2-ylmethoxy)-3-trifluoromethyl-pyrazine-2-carboxylic acid (2-cyclopropyl-2-hydroxy-propyl)-amide, and all pharmaceutically acceptable salts thereof.

Especially preferred is a compound of formula I that is 6-(4-chloro-phenyl)-5-cyclopropylmethoxy-3-trifluoromethyl-pyrazine-2-carboxylic acid ((1R,2R)-2-hydroxy-cyclohexyl)-amide.

The compounds of formula I of the invention can be prepared by a process, which process comprises:
coupling a compound of formula

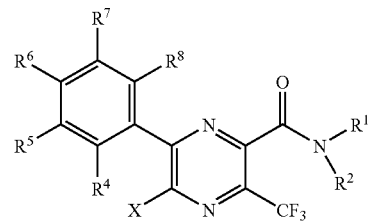

wherein X is halogen and $R^1$, $R^2$ and $R^4$ to $R^8$ are as defined herein before, with an alcohol of the formula $R^3$—OH    III wherein $R^3$ is as defined herein before, in the presence of a suitable base, and, if desired, converting the resulting compound of formula I into a pharmaceutically acceptable salt thereof.

The suitable base can be selected from the group consisting of alkylmetal compounds, alkalimetal hydrides and alkalimetal carbonates. Preferred alkalimetal compounds are n-butyllithium or t-butyllithium. Preferably, the alkalimetal hydride is sodium hydride. Preferred alkalimetal carbonate is cesium carbonate. X is halogen, preferably X is bromo.

Thus, the compounds of formula I can be manufactured by the methods given in the examples and according to the synthesis as described in scheme 1 below. Starting materials are either commercially available or can be prepared by methods analogous to the methods given below or in the examples or by methods known in the art.

Scheme 1

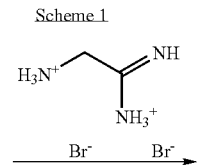
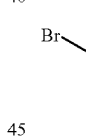
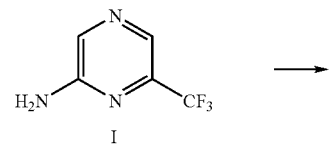
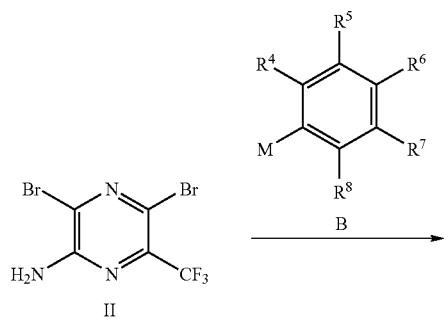
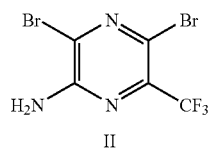

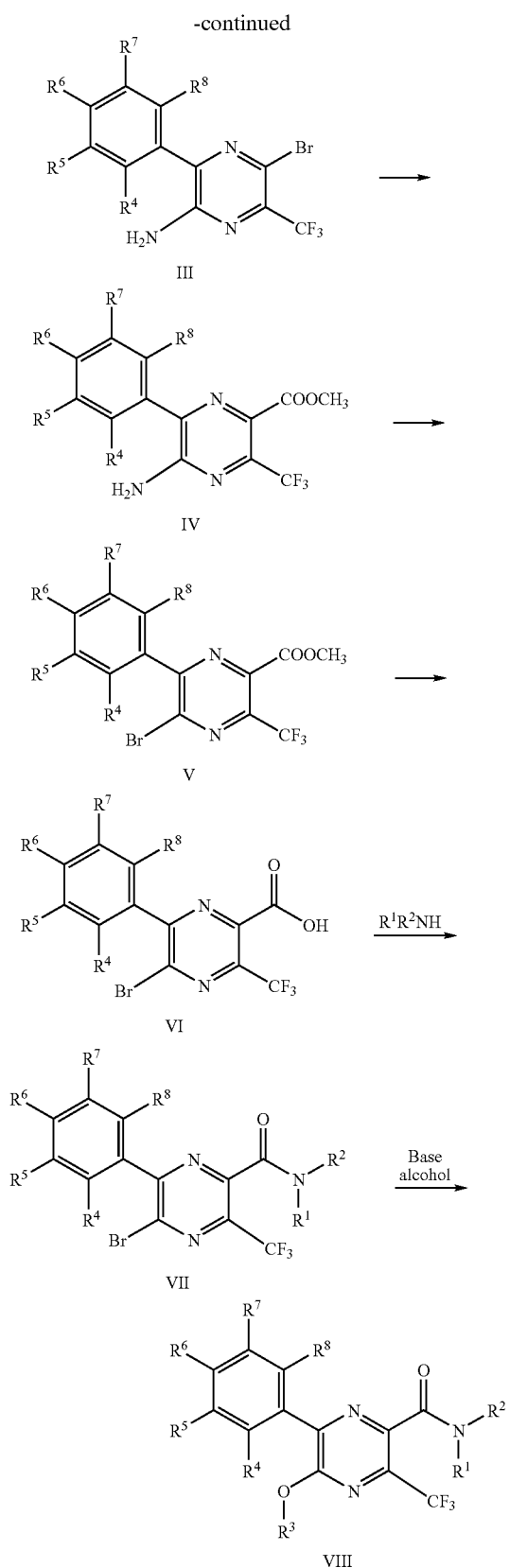

from 3,3-dibromo-1,1,1-trifluoro-propan-2-one and 2-amino-acetamidine dihydrobromide by first reacting 3,3-dibromo-1,1,1-trifluoro-propan-2-one with sodium acetate and then condensing with 2-amino-acetamidine dihydrobromide (U.S. Pat. No. 4,293,552).

Compound II can be obtained from compound I by reaction with brominating agents such as bromine, N-bromosuccinimide or the complex of bromine with pyridine preferably N-bromosuccinimide in an inert solvent, preferably water.

Compounds of the general formula III can be obtained from compound II by reaction with a suitably substituted aryl metal species of formula B, preferably an arylboronic acid or arylboronic acid ester, in the presence of a suitable catalyst, preferably a palladium catalyst and more preferably palladium(II)acetate/triphenyl-phosphine mixtures or palladium (II)chloride-dppf (1,1'-bis(diphenylphosphino)-ferrocene) complexes or tetrakis(triphenylphosphine)palladium (0) and a base, preferably aqueous sodium carbonate in an inert solvent such as dimethylformamide, toluene or more preferably 2,2'dimethoxyethane at temperatures ranging from room temperature or more preferably at reflux. Reaction preferentially occurs at the bromine atom neighboring the amino group.

Compounds of the general formula IV can be obtained from compounds of the general formula III by palladium (II), preferably palladium(II) acetate catalyzed carbonylation in the presence of a suitable base such as a tertiary amine base, preferably triethylamine in a suitable solvent such as an alcohol, preferably methanol.

Compounds of the general formula V can be obtained from compounds of the general formula IV by reaction with nitrosating agents such as a metal nitrite or an organic nitrite more preferably isoamylnitrite, in the presence of a bromide source such as hydrobromic acid or more preferably trimethylbromosilane in a suitable solvent such as halogenated hydrocarbons more preferably dibromomethane.

Compounds of the general formula VI can then be obtained by saponification of compounds of the general formula V by methods known in the art, for example by saponification with an alkalimetal hydroxide, for example lithium hydroxide, in a suitable solvent, for example a mixture of tetrahydrofuran (THF) and water.

In the following step compounds of the general formula VII are obtained from compounds of the general formula VI and the corresponding amine of formula $R^1R^2NH$ by suitable amide bond forming reactions. These reactions are known in the art. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformations. A convenient method is to use 1-chloro-N,N,2-trimethylpropenylamine, activating compounds of the general formula VI by forming their acid chlorides and then reacting with a corresponding amine of the general formula $R^1R^2NH$ in the presence of a suitable base such as a tertiary amine base such as triethylamine more preferably Huenig's base.

Compounds of the general formula VIII can be obtained from compounds of the general formula VII by reaction with corresponding aliphatic or aromatic alcohols such as trifluoroethanol, cyclopropylmethanol, pyridin-2-yl-methanol or phenol in the presence of a suitable base such as an alkylmetal compound, preferably butyllithium, alkalimetal hydrides, Following the procedure according to scheme 1, compound I (6-trifluoromethyl-pyrazin-2-ylamine) can be used as starting material. I can be prepared by a two step sequence preferably sodium hydride or alkali metal carbonates, preferably cesium carbonate in a suitable solvent such as tetrahydrofuran, dimethylformamide, dimethylsufoxide or the reacting alcohol itself at temperatures ranging from 0° C. to reflux, preferably at 0° C. to room temperature, or at reflux of the corresponding alcohol (e.g. trifloroethanol).

As described above, the compounds of formula I of the present invention can be used as medicaments for the treatment and/or prophylaxis of diseases which can be treated with HDL-cholesterol raising agents. "Diseases which can be treated with HDL-cholesterol raising agents" means such diseases as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. Preferably, such diseases are atherosclerosis, peripheral vascular disease and dyslipidemia. Most preferably, the disease is dyslipidemia.

The invention therefore also relates to a pharmaceutical composition comprising a compound as defined above and a pharmaceutically acceptable carrier and/or adjuvant which is useful for the treatment and/or prophylaxis of diseases which can be treated with HDL-cholesterol raising agents.

Thus, the invention relates to a pharmaceutical composition as defined above for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I to a patient in need thereof.

In addition, the invention relates to the use of compounds of formula I as defined above for the preparation of a medicament for the treatment and/or prophylaxis of diseases that can be treated with HDL raising agents.

In addition, the compounds of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is preferred.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1 to 100 mg, preferably 5 to 50 mg, of a compound of formula I.

The following tests were carried out in order to determine the activity of the compounds of formula I and their valuable pharmacological properties.

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 µl/L of b-mercaptoethanol, RPMI-1640 medium. Cells are washed once with RPMI-1640 and loaded with RPMI-1640 medium containing 2% FCS, 50 µg/ml acetylated LDL, and 10 µCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 μg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and $EC_{50}$ values were determined.

The compounds of the present invention exhibit $EC_{50}$ values in a range of 0.01 μM to 2.0 μM in the cholesterol efflux assay. Preferably, the compounds of the present invention have $EC_{50}$ values in a range of 0.01 μM to 1.2 μM; more preferably 0.01 μM to 0.6 μM. Representative compounds with their corresponding $EC_{50}$ values in the cholesterol efflux assay are shown below:

| Example | $EC_{50}$ [μM] |
| --- | --- |
| 1 | 0.61 |
| 2 | 0.57 |
| 3 | 0.72 |

Affinity Towards Cannabinoid CB1 Receptor

The affinity of the compounds of formula I of the present invention towards cannabinoid CB1 receptors was determined as described in WO 2007/147746, page 31. Surprisingly, the compounds of the present invention show only poor affinity for the CB1 receptor compared to the compounds of WO 2007/147746. They possess affinities above 1 μM and more preferably above 3 μM.

Further demonstration of biological activities of the compounds of the present invention may be accomplished through the following in vivo assays that are well known in the art.

Effects on Plasma Lipid Levels in Lean, Chow Fed Rats

Effects of compounds of compounds of formula I on plasma lipid levels were determined in lean, chow-fed Sprague-Dawley rats with compounds administered by p.o. gavage. After one week of acclimation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g. liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using calorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was also determined in cholesterol/fat fed hamsters. The protocol is identical as described above except that animals are fed with chow diet enriched with 10% (w/w) saturated fat and 0.05% (w/w) cholesterol. Animals received this high fat diet 2 weeks before starting compound administration and continued this diet throughout the study. The 2 weeks pre-treatment induced an increase in plasma cholesterol and triglyceride levels allowing a better assessment of LDL-C and triglyceride changes.

EXAMPLES

Example 1

Preparation of 6-(4-chloro-phenyl)-5-cyclopropylmethoxy-3-trifluoromethyl-pyrazine-2-carboxylic acid ((1R,2R)-2-hydroxy-cyclohexyl)-amide To 0.048 g 5-bromo-6-(4-chloro-phenyl)-3-trifluoromethyl-pyrazine-2-carboxylic acid ((1R,2R)-2-hydroxy-cyclohexyl)-amide was added 1 ml of a 0.25 M solution of lithium cyclopropylmethoxide in tetrahydrofuran and the mixture was stirred at room temperature for 30 min. The orange reaction mixture was partitioned between 10% citric acid and ethyl acetate. The phases were separated and the organic phase was washed with brine. After evaporation the crystalline residue was triturated under methanol to yield 0.028 g of the title compound as white crystals. MS (M−H) at 468.2.

The starting materials were prepared as follows:

Example 1b

Preparation of 5-bromo-6-(4-chloro-phenyl)-3-trifluoromethyl-pyrazine-2-carboxylic acid ((1R,2R)-2-hydroxy-cyclohexyl)-amide To a yellow suspension of 1.50 g 5-bromo-6-(4-chloro-phenyl)-3-trifluoromethyl-pyrazine-2-carboxylic acid in 11 ml dichloromethane was added drop wise 0.608 g 1-chloro-N,N, 2-trimethylpropenylamine and the resulting the yellow solution was stirred at room temperature for 30 min. The resulting orange solution was added dropwise to a cooled (ice bath) solution of 0.522 g (1R,2R)-2-amino-cyclohexanol and 0.7868 g ethyldiisopropylamine in 10 ml ethyl acetate. This red solution was stirred at room temperature for 90 min. To the red solution was added 30 ml 10% aqueous citric acid solution. The layers were separated and the organic layer was purified by chromatography on silica gel with a gradient of heptane: ethyl acetate=1:1 to ethyl acetate to yield 1.56 g of the title compound as yellow crystals. MS (M−H) at 479.0 and 476.0.

Example 1c

Preparation of 5-bromo-6-(4-chloro-phenyl)-3-trifluoromethyl-pyrazine-2-carboxylic acid To a solution of 7.7 g 5-bromo-6-(4-chloro-phenyl)-3-trifluoromethyl-pyrazine-2-carboxylic acid methyl ester in 50 ml tetrahydrofuran was added at 0° C. 20 ml of a 1M solution of lithium hydroxide in water. The cooling bath was removed and the mixture was stirred at ambient temperature for 20 min. The orange reaction mixture was partitioned between heptane and water. The phases were separated the aqueous phase was mixed with ethyl acetate and 10% aqueous citric acid whereby the yellow orange color almost disappeared. The phases were separated and the organic phase was washed with brine dried over sodium sulfate, evaporated and dried under high vacuum to yield 5.54 g of the title compound as yellow solid. This material was recrystallized from ethyl acetate/heptane before use. MS (M−H) at 381.1 and 379.1.

Example 1d

Preparation of 5-bromo-6-(4-chloro-phenyl)-3-trifluoromethyl-pyrazine-2-carboxylic acid methyl ester To a suspension of 2.11 g 5-amino-6-(4-chloro-phenyl)-3-trifluoromethyl-pyrazine-2-carboxylic acid methyl ester in 20 ml dibromomethane was added 1.59 g isoamylnitrite and the mixture was cooled to 0° C. To the resulting suspension was added 2.922 g trimethylbromosilane and the mixture was stirred at 0° C. for 10 min (no conversion by HPLC) and at room temperature for 3 h. To the dark reaction mixture was added another 1.59 g isoamylnitrite and the mixture was stirred at room temperature for 6 h. The dark reaction mixture was pored onto ice and ca 20 ml 10% sodium bicarbonate and the product was extracted with dichloromethane (2.64 g raw material which crystallized) and purified by chromatography on silica gel (20 g hep:EE=9:1 to 1:1) to yield 2.290 g of the title compound as white crystals. MS (M+H at 396.8 and 394.9).

Example 1e

Preparation of 5-amino-6-(4-chloro-phenyl)-3-trifluoromethyl-pyrazine-2-carboxylic acid methyl ester A mixture of 12.57 g 5-bromo-3-(4-chloro-phenyl)-6-trifluoromethyl-pyrazin-2-ylamine, 0.60 g palladium(II)chloride-dppf-dichloromethane complex, 75 ml methanol, 75 ml ethyl acetate and 10.0 ml triethylamine was heated to 110° C. in an autoclav under 70 bar of carbon monoxide for 20 h. The solvents were evaporated and the residue was purified by chromatography on silica gel with dichloromethane to yield 6.48 g of the title compound as off white solid. MS (M−H) at 330.1.

Example 1f

Preparation of 5-bromo-3-(4-chloro-phenyl)-6-trifluoromethyl-pyrazin-2-ylamine

To a mixture of 6.08 g 3,5-dibromo-6-trifluoromethyl-pyrazin-2-ylamine, 3.25 g 4-chlorophenylboronic acid and 1.095 g tetrakis(triphenylphosphine)palladium(0) in 60 ml 1,2-dimethoxyethane was added a solution of 4.016 g sodium carbonate in 22.74 ml water and the mixture was heated to reflux for 18 h. The reaction mixture was cooled to room temperature and partitioned between 10% aqueous citric acid and ethyl acetate, the phases were separated and the organic phase was purified by chromatography on silica gel with a gradient of 9:1 heptane: dichloromethane to 1:1 heptane: dichloromethane to yield 4.45 g of the title compound as white solid. MS (M−H) at 352.0 and 350.1.

Example 1g

Preparation of 3,5-dibromo-6-trifluoromethyl-pyrazin-2-ylamine

To a solution of 22.5 g sodium acetate in 230 ml water was added 21.5 g 3,3-dibromo-1,1,1-trifluoropropanone at reflux and the mixture was refluxed for 10 min. The resulting solution was cooled to 0° C. in an acetone ice bath and added dropwise to a suspension of 19.5 g aminoacetamidine dihydrobromide in 250 ml methanol at −30° C. (dry ice acetone cooling) so that the temperature did not rise above −30° C. during the addition. To the resulting solution was added dropwise a solution of 12.285 g sodium hydroxide in 100 ml water. The mixture was then allowed to warm to room temperature (warm water bath) and then stirred at room temperature for 3 h. The dark reaction mixture was concentrated under aspirator vacuum to remove methanol and extracted with ethyl acetate (4 times). The phases were separated and the organic phase was washed with brine, treated with charcoal and dried with sodium sulfate and evaporated. To the concentrated yellow solution was added heptane and the mixture was seeded whereby crystallization was initiated. The mixture was stirred at room temperature to complete crystallization. The solid was collected by filtration to yield 8.81 g of the title compound as light yellow crystals. The aqueous layers were kept at room temperature for 72 h and then extracted (2 times) with ethyl acetate. The combined organic layers were treated with charcoal and sodium sulfate and evaporated. The residue was taken up in dichloromethane and heptane was added. The mixture was concentrated again until crystallization occurred. The solid was collected by filtration to yield another 2.06 g of the title compound as light yellow crystals. MS (M−H) at 162.1.

Example 2

Preparation of 6-(4-chloro-phenyl)-5-(2,2,2-trifluoro-ethoxy)-3-trifluoromethyl-pyrazine-2-carboxylic acid (2-cyclopropyl-2-hydroxy-propyl)-amide A mixture of 0.050 g 5-bromo-6-(4-chloro-phenyl)-3-trifluoromethyl-pyrazine-2-carboxylic acid (2-cyclopropyl-2-hydroxy-propyl)-amide and 0.050 g cesium carbonate in 0.5 ml trifluoroethanol was heated to 80° C. for 20 min. The reaction mixture was partitioned between 10% citric acid and ethyl acetate. The phases were separated and the organic phase was washed with brine evaporated and the crystalline residue was triturated under heptane to yield 0.040 g of the title compound as off white powder. MS (M–H) at 496.4 and 498.4.

The starting material was prepared as follows:

Example 2b

Preparation of 5-bromo-6-(4-chloro-phenyl)-3-trifluoromethyl-pyrazine-2-carboxylic acid (2-cyclopropyl-2-hydroxy-propyl)-amide In analogy to example 1b (5-bromo-6-(4-chloro-phenyl)-3-trifluoromethyl-pyrazine-2-carboxylic acid (2-cyclopropyl-2-hydroxy-propyl)-amide), the title compound was obtained by substituting leucinol with 1-amino-2-cyclopropyl-propan-2-ol.

Example 3

Preparation of 6-(4-chloro-phenyl)-5-cyclopropylmethoxy-3-trifluoromethyl-pyrazine-2-carboxylic acid (2-cyclopropyl-2-hydroxy-propyl)-amide To a solution of 0.048 g 5-bromo-6-(4-chloro-phenyl)-3-trifluoromethyl-pyrazine-2-carboxylic acid (2-cyclopropyl-2-hydroxy-propyl)-amide in 0.3 ml dimethylsulfoxide was added 0.2 ml of a 1M solution of cyclopropylmethoxide in dimethylsulfoxide and the mixture was stirred at room temperature for 30 min. The orange reaction mixture was partitioned between 10% citric acid and ethyl acetate. The phases were separated and the organic phase was purified by chromatography on silica gel with heptane: ethyl acetate=9:1 to 1:1 to yield 0.015 g of the title compound as white solid. MS (M+H) at 468.3.

Example 4

Preparation of 6-(3-chloro-phenyl)-5-(2,2,2-trifluoro-ethoxy)-3-trifluoromethyl-pyrazine-2-carboxylic acid ((1R,2R)-2-hydroxy-cyclohexyl)-amide In analogy to example 2 (6-(4-chloro-phenyl)-5-(2,2,2-trifluoro-ethoxy)-3-trifluoromethyl-pyrazine-2-carboxylic acid (2-cyclopropyl-2-hydroxy-propyl)-amide the title compound was obtained by substituting 5-bromo-6-(4-chloro-phenyl)-3-trifluoromethyl-pyrazine-2-carboxylic acid (2-cyclopropyl-2-hydroxy-propyl)-amide with 5-bromo-6-(3-chloro-phenyl)-3-trifluoromethyl-pyrazine-2-carboxylic acid ((1R,2R)-2-hydroxy-cyclohexyl)-amide.

The starting material was prepared as follows:

Example 4b

Preparation of 5-bromo-6-(3-chloro-phenyl)-3-trifluoromethyl-pyrazine-2-carboxylic acid ((1R,2R)-2-hydroxy-cyclohexyl)-amide This compound was prepared in analogy to example 1b (5-bromo-6-(4-chloro-phenyl)-3-trifluoromethyl-pyrazine-2-carboxylic acid ((1R,2R)-2-hydroxy-cyclohexyl)-amide) by substituting 5-bromo-6-(4-chloro-phenyl)-3-trifluoromethyl-pyrazine-2-carboxylic acid with 5-bromo-6-(3-chloro-phenyl)-3-trifluoromethyl-pyrazine-2-carboxylic acid. MS (M–H) at 477.9 and 476.0.

Example 5

Preparation of 6-(3-chloro-phenyl)-5-(2,2,2-trifluoro-ethoxy)-3-trifluoromethyl-pyrazine-2-carboxylic acid (2-cyclopropyl-2-hydroxy-propyl)-amide The title compound was obtained in analogy to example 2 (6-(4-Chloro-phenyl)-5-(2,2,2-trifluoro-ethoxy)-3-trifluoromethyl-pyrazine-2-carboxylic acid (2-cyclopropyl-2-hydroxy-propyl)-amide) by substituting 5-bromo-6-(4-chloro-phenyl)-3-trifluoromethyl-pyrazine-2-carboxylic acid (2-cyclopropyl-2-hydroxy-propyl)-amide with 5-bromo-6-(3-chloro-phenyl)-3-trifluoromethyl-pyrazine-2-carboxylic acid (2-cyclopropyl-2-hydroxy-propyl)-amide.

The starting material was prepared as follows:

Example 5b

Preparation of 5-bromo-6-(3-chloro-phenyl)-3-trifluoromethyl-pyrazine-2-carboxylic acid (2-cyclopropyl-2-hydroxy-propyl)-amide In analogy to example 1b the title compound was prepared from 5-bromo-6-(3-chloro-phenyl)-3-trifluoromethyl-pyrazine-2-carboxylic acid and racemic leucinol.

Example 6

Preparation of 6-(3-chloro-phenyl)-5-cyclopropylmethoxy-3-trifluoromethyl-pyrazine-2-carboxylic acid ((1R,2R)-2-hydroxy-cyclohexyl)-amide The title compound was obtained in analogy to example 1 (6-(4-chloro-phenyl)-5-cyclopropylmethoxy-3-trifluoromethyl-pyrazine-2-carboxylic acid ((1R,2R)-2-hydroxy-cyclohexyl)-amide) by substituting 5-bromo-6-(4-chloro-phenyl)-3-trifluoromethyl-pyrazine-2-carboxylic acid ((1R,2R)-2-hydroxy-cyclohexyl)-amide with 5-bromo-6-(3-chloro-phenyl)-3-trifluoromethyl-pyrazine-2-carboxylic acid ((1R,2R)-2-hydroxy-cyclohexyl)-amide.

Example 7

Preparation of 6-(3-chloro-phenyl)-5-cyclopropylmethoxy-3-trifluoromethyl-pyrazine-2-carboxylic acid (2-cyclopropyl-2-hydroxy-propyl)-amide In analogy to example 3 (6-(4-chloro-phenyl)-5-cyclopropylmethoxy-3-trifluoromethyl-pyrazine-2-carboxylic acid (2-cyclopropyl-2-hydroxy-propyl)-amide) the title compound was prepared by substituting 5-bromo-6-(4-chlorophenyl)-3-trifluoromethyl-pyrazine-2-carboxylic acid (2-cyclopropyl-2-hydroxy-propyl)-amide with 5-bromo-6-(3-chloro-phenyl)-3-trifluoromethyl-pyrazine-2-carboxylic acid (2-cyclopropyl-2-hydroxy-propyl)-amide.

Example 8

Preparation of 6-(3-chloro-phenyl)-5-phenoxy-3-trifluoromethyl-pyrazine-2-carboxylic acid ((1R,2R)-2-hydroxy-cyclohexyl)-amide In analogy to example 1 (6-(4-chloro-phenyl)-5-cyclopropylmethoxy-3-trifluoromethyl-pyrazine-2-carboxylic acid ((1R,2R)-2-hydroxy-cyclohexyl)-amide) the title compound was obtained by substituting 5-bromo-6-(4-chloro-phenyl)-3-trifluoromethyl-pyrazine-2-carboxylic acid ((1R,2R)-2-hydroxy-cyclohexyl)-amide with 5-bromo-6-(3-chloro-phenyl)-3-trifluoromethyl-pyrazine-2-carboxylic acid ((1R,2R)-2-hydroxy-cyclohexyl)-amide and cyclopropylmethanol with phenol.

Example 9

Preparation of 6-(3-chloro-phenyl)-5-phenoxy-3-trifluoromethyl-pyrazine-2-carboxylic acid (2-cyclopropyl-2-hydroxy-propyl)-amide In analogy to example 3 (6-(4-chloro-phenyl)-5-cyclopropylmethoxy-3-trifluoromethyl-pyrazine-2-carboxylic acid (2-cyclopropyl-2-hydroxy-propyl)-amide) the title compound was obtained by substituting 5-bromo-6-(4-chloro-phenyl)-3-trifluoromethyl-pyrazine-2-carboxylic acid (2-cyclopropyl-2-hydroxy-propyl)-amide with 5-bromo-6-(3-chloro-phenyl)-3-trifluoromethyl-pyrazine-2-carboxylic acid (2-cyclopropyl-2-hydroxy-propyl)-amide and cyclopropylmethanol with phenol.

Example 10

Preparation of 6-(3-chloro-phenyl)-5-(pyridin-2-ylmethoxy)-3-trifluoromethyl-pyrazine-2-carboxylic acid ((1R,2R)-2-hydroxy-cyclohexyl)-amide In analogy to example 1 (6-(4-chloro-phenyl)-5-cyclopropylmethoxy-3-trifluoromethyl-pyrazine-2-carboxylic acid ((1R,2R)-2-hydroxy-cyclohexyl)-amide) this compound was prepared by substituting 5-bromo-6-(4-chloro-phenyl)-3-trifluoromethyl-pyrazine-2-carboxylic acid ((1R,2R)-2-hydroxy-cyclohexyl)-amide with 5-bromo-6-(3-chloro-phenyl)-3-trifluoromethyl-pyrazine-2-carboxylic acid ((1R,2R)-2-hydroxy-cyclohexyl)-amide and cyclopropylmethanol with pyridin-2-yl-methanol.

Example 11

Preparation of 6-(3-chloro-phenyl)-5-(pyridin-2-ylmethoxy)-3-trifluoromethyl-pyrazine-2-carboxylic acid (2-cyclopropyl-2-hydroxy-propyl)-amide In analogy to example 3 (6-(4-chloro-phenyl)-5-cyclopropylmethoxy-3-trifluoromethyl-pyrazine-2-carboxylic acid (2-cyclopropyl-2-hydroxy-propyl)-amide) the title compound was obtained by substituting 5-bromo-6-(4-chloro-phenyl)-3-trifluoromethyl-pyrazine-2-carboxylic acid (2-cyclopropyl-2-hydroxy-propyl)-amide with 5-bromo-6-(3-chloro-phenyl)-3-trifluoromethyl-pyrazine-2-carboxylic acid (2-cyclopropyl-2-hydroxy-propyl)-amide and cyclopropylmethanol with pyridin-2-yl-methanol.

Example 12

Preparation of 6-(3,4-dichloro-phenyl)-5-(2,2,2-trifluoro-ethoxy)-3-trifluoromethyl-pyrazine-2-carboxylic acid ((1R,2R)-2-hydroxy-cyclohexyl)-amide In analogy to example 4 (6-(3-chloro-phenyl)-5-(2,2,2-trifluoro-ethoxy)-3-trifluoromethyl-pyrazine-2-carboxylic acid ((1R,2R)-2-hydroxy-cyclohexyl)-amide) the title compound was prepared by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 13

Preparation of 6-(3,4-dichloro-phenyl)-5-(2,2,2-trifluoro-ethoxy)-3-trifluoromethyl-pyrazine-2-carboxylic acid (2-cyclopropyl-2-hydroxy-propyl)-amide This compound was obtained in analogy to example 5 (6-(3-chloro-phenyl)-5-(2,2,2-trifluoro-ethoxy)-3-trifluoromethyl-pyrazine-2-carboxylic acid (2-cyclopropyl-2-hydroxy-propyl)-amide) by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 14

Preparation of 6-(3,4-dichloro-phenyl)-5-cyclopropylmethoxy-3-trifluoromethyl-pyrazine-2-carboxylic acid ((1R,2R)-2-hydroxy-cyclohexyl)-amide In analogy to example 6 (6-(3-chloro-phenyl)-5-cyclopropylmethoxy-3-trifluoromethyl-pyrazine-2-carboxylic acid ((1R,2R)-2-hydroxy-cyclohexyl)-amide) the title compound was obtained by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 15

Preparation of 6-(3,4-dichloro-phenyl)-5-cyclopropylmethoxy-3-trifluoromethyl-pyrazine-2-carboxylic acid (2-cyclopropyl-2-hydroxy-propyl)-amide In analogy to example 7 (3-chloro-phenyl)-5-cyclopropylmethoxy-3-trifluoromethyl-pyrazine-2-carboxylic acid (2-cyclopropyl-2-hydroxy-propyl)-amide) the title compound was prepared by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 16

Preparation of 6-(3,4-dichloro-phenyl)-5-phenoxy-3-trifluoromethyl-pyrazine-2-carboxylic acid ((1R,2R)-2-hydroxy-cyclohexyl)-amide The title compound was prepared in analogy to example 8 (6-(3-chloro-phenyl)-5-phenoxy-3-trifluoromethyl-pyrazine-2-carboxylic acid ((1R,2R)-2-hydroxy-cyclohexyl)-amide) by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 17

Preparation of 6-(3,4-dichloro-phenyl)-5-phenoxy-3-trifluoromethyl-pyrazine-2-carboxylic acid (2-cyclopropyl-2-hydroxy-propyl)-amide In analogy to example 9 (6-(3-chloro-phenyl)-5-phenoxy-3-trifluoromethyl-pyrazine-2-carboxylic acid (2-cyclopropyl-2-hydroxy-propyl)-amide) the title compound was obtained by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 18

Preparation of 6-(3,4-dichloro-phenyl)-5-(pyridin-2-ylmethoxy)-3-trifluoromethyl-pyrazine-2-carboxylic acid ((1R,2R)-2-hydroxy-cyclohexyl)-amide In analogy to example 6 (6-(3-chloro-phenyl)-5-cyclopropylmethoxy-3-trifluoromethyl-pyrazine-2-carboxylic acid ((1R,2R)-2-hydroxy-cyclohexyl)-amide) this compound was prepared by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 19

Preparation of 6-(3,4-dichloro-phenyl)-5-(pyridin-2-ylmethoxy)-3-trifluoromethyl-pyrazine-2-carboxylic acid (2-cyclopropyl-2-hydroxy-propyl)-amide In analogy to example 7 (6-(3-chloro-phenyl)-5-cyclopropylmethoxy-3-trifluoromethyl-pyrazine-2-carboxylic acid (2-cyclopropyl-2-hydroxy-propyl)-amide) the title compound was obtained by substituting 5-bromo-6-(3-chloro-phenyl)-3-trifluoromethyl-pyrazine-2-carboxylic acid methyl ester with 5-bromo-6-(3,4-dichloro-phenyl)-3-trifluoromethyl-pyrazine-2-carboxylic acid methyl ester.

Example 20

Preparation of 6-(4-methanesulfonylamino-phenyl)-5-(2,2,2-trifluoro-ethoxy)-3-trifluoromethyl-pyrazine-2-carboxylic acid ((1R,2R)-2-hydroxy-cyclohexyl)-amide The title compound was prepared in analogy to example 4 (6-(3-chloro-phenyl)-5-(2,2,2-trifluoro-ethoxy)-3-trifluoromethyl-pyrazine-2-carboxylic acid ((1R,2R)-2-hydroxy-cyclohexyl)-amide) by substituting 5-bromo-3-(3-chloro-phenyl)-6-trifluoromethyl-pyrazin-2-ylamine by N-[4-(3-amino-6-bromo-5-trifluoromethyl-pyrazin-2-yl)-phenyl]-methanesulfonamide.

Example 21

Preparation of 6-(4-methanesulfonylamino-phenyl)-5-(2,2,2-trifluoro-ethoxy)-3-trifluoromethyl-pyrazine-2-carboxylic acid (2-cyclopropyl-2-hydroxy-propyl)-amide This compound was prepared in analogy to example 5 (6-(3-chloro-phenyl)-5-(2,2,2-trifluoro-ethoxy)-3-trifluoromethyl-pyrazine-2-carboxylic acid (2-cyclopropyl-2-hydroxy-propyl)-amide) by substituting 5-bromo-3-(3-chloro-phenyl)-6-trifluoromethyl-pyrazin-2-ylamine by N-[4-(3-amino-6-bromo-5-trifluoromethyl-pyrazin-2-yl)-phenyl]-methanesulfonamide.

Example 22

Preparation of 6-(4-methanesulfonylamino-phenyl)-5-cyclopropylmethoxy-3-trifluoromethyl-pyrazine-2-carboxylic acid ((1R,2R)-2-hydroxy-cyclohexyl)-amide In analogy to example 6 (6-(3-chloro-phenyl)-5-cyclopropylmethoxy-3-trifluoromethyl-pyrazine-2-carboxylic acid ((1R,2R)-2-hydroxy-cyclohexyl)-amide) the title compound was prepared by substituting 5-bromo-3-(3-chloro-phenyl)-6-trifluoromethyl-pyrazin-2-ylamine with N-[4-(3-amino-6-bromo-5-trifluoromethyl-pyrazin-2-yl)-phenyl]-methanesulfonamide.

Example 23

Preparation of 6-(4-methanesulfonylamino-phenyl)-5-cyclopropylmethoxy-3-trifluoromethyl-pyrazine-2-carboxylic acid (2-cyclopropyl-2-hydroxy-propyl)-amide In analogy to example 7 (6-(3-chloro-phenyl)-5-cyclopropylmethoxy-3-trifluoromethyl-pyrazine-2-carboxylic acid (2-cyclopropyl-2-hydroxy-propyl)-amide) the title compound was obtained by substituting 5-bromo-3-(3-chloro-phenyl)-6-trifluoromethyl-pyrazin-2-ylamine with N-[4-(3-amino-6-bromo-5-trifluoromethyl-pyrazin-2-yl)-phenyl]-methanesulfonamide.

Example 24

Preparation of 6-(4-methanesulfonylamino-phenyl)-5-phenoxy-3-trifluoromethyl-pyrazine-2-carboxylic acid ((1R,2R)-2-hydroxy-cyclohexyl)-amide In analogy to example 8 (6-(3-chloro-phenyl)-5-phenoxy-3-trifluoromethyl-pyrazine-2-carboxylic acid ((1R,2R)-2-hydroxy-cyclohexyl)-amide) this compound was obtained by substituting 5-bromo-3-(3-chloro-phenyl)-6-trifluoromethyl-pyrazin-2-ylamine with N-[4-(3-amino-6-bromo-5-trifluoromethyl-pyrazin-2-yl)-phenyl]-methanesulfonamide.

Example 25

Preparation of 6-(4-methanesulfonylamino-phenyl)-5-phenoxy-3-trifluoromethyl-pyrazine-2-carboxylic acid (2-cyclopropyl-2-hydroxy-propyl)-amide In analogy to example 9 (6-(3-chloro-phenyl)-5-phenoxy-3-trifluoromethyl-pyrazine-2-carboxylic acid (2-cyclopropyl-2-hydroxy-propyl)-amide) the title compound was obtained by substituting 5-bromo-3-(3-chloro-phenyl)-6-trifluoromethyl-pyrazin-2-ylamine with N-[4-(3-amino-6-bromo-5-trifluoromethyl-pyrazin-2-yl)-phenyl]-methanesulfonamide.

Example 26

Preparation of 6-(4-methanesulfonylamino-phenyl)-5-(pyridin-2-ylmethoxy)-3-trifluoromethyl-pyrazine-2-carboxylic acid ((1R,2R)-2-hydroxy-cyclohexyl)-amide In analogy to example 6 (6-(3-chloro-phenyl)-5-cyclopropylmethoxy-3-trifluoromethyl-pyrazine-2-carboxylic acid ((1R,2R)-2-hydroxy-cyclohexyl)-amide) the title compound was prepared by substituting 5-bromo-3-(3-chloro-phenyl)-6-trifluoromethyl-pyrazin-2-ylamine with N-[4-(3-amino-6-bromo-5-trifluoromethyl-pyrazin-2-yl)-phenyl]-methanesulfonamide.

Example 27

Preparation of 6-(4-methanesulfonylamino-phenyl)-5-(pyridin-2-ylmethoxy)-3-trifluoromethyl-pyrazine-2-carboxylic acid (2-cyclopropyl-2-hydroxy-propyl)-amide This compound was prepared in analogy to example 7 (6-(3-chloro-phenyl)-5-cyclopropylmethoxy-3-trifluoromethyl-pyrazine-2-carboxylic acid (2-cyclopropyl-2-hydroxy-propyl)-amide) by substituting 5-bromo-3-(3-chloro-phenyl)-6-trifluoromethyl-pyrazin-2-ylamine with N-[4-(3-amino-6-bromo-5-trifluoromethyl-pyrazin-2-yl)-phenyl]-methanesulfonamide.

Example 28

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example 29

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 30

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula I:

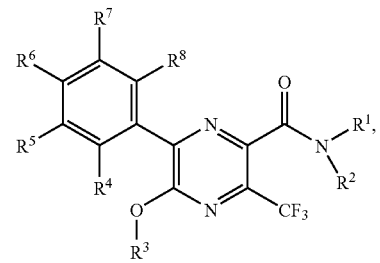

or a pharmaceutically acceptable salt thereof, wherein:
$R^1$ is selected from the group consisting of:
 (1) cycloalkyl, which is unsubstituted or substituted by hydroxy or lower hydroxyalkyl, and
 (2) —$CH_2$—$CR^9R^{10}$-cycloalkyl, wherein $R^9$ is hydrogen or lower alkyl, and $R^{10}$ is hydrogen or hydroxy;
$R^2$ is hydrogen;
$R^3$ is selected from the group consisting of:
 (1) lower cycloalkylalkyl,
 (2) lower alkoxyalkyl,
 (3) lower halogenalkyl,
 (4) lower heteroarylalkyl, wherein the heteroaryl group is unsubstituted or substituted once or twice by lower alkyl, and
 (5) phenyl, which is unsubstituted or substituted once or twice by halogen;
$R^4$ and $R^8$ independently from each other are hydrogen or halogen; and
$R^5$, $R^6$ and $R^7$ independently from each other are selected from the group consisting of:
 (1) hydrogen,
 (2) lower alkyl,
 (3) lower alkoxy, (4) halogen,
(5) lower halogenalkyl,
(6) lower halogenalkoxy,
(7) lower alkylsulfonylamino, and
(8) cyano.

2. A compound of formula I according to claim 1, wherein $R^3$ is selected from the group consisting of lower cycloalkylalkyl, lower halogenalkyl and lower heteroarylalkyl, wherein the heteroaryl group is unsubstituted or mono- or di-substituted by lower alkyl.

3. A compound according to claim 1, wherein $R^3$ is lower halogenalkyl.

4. A compound according to claim 1, wherein $R^3$ is lower cycloalkylalkyl.

5. A compound according to claim 1, wherein $R^3$ is lower heteroarylalkyl, wherein the heteroaryl group is unsubstituted or mono- or di-substituted by lower alkyl.

6. A compound according to claim 1, wherein $R^3$ is phenyl.

7. A compound according to claim 1, wherein $R^1$ is cycloalkyl substituted by hydroxy.

8. A compound according to claim 1, wherein $R^1$ is —CH$_2$—CR$^9$R$^{10}$-cycloalkyl and wherein $R^9$ is methyl and $R^{10}$ is hydroxy.

9. A compound according to claim 1, wherein at least one of $R^5$, $R^6$ and $R^7$ is selected from the group consisting of lower alkyl, halogen, lower halogenalkyl, lower halogenalkoxy, lower alkylsulfonylamino and cyano.

10. A compound according to claim 1, wherein at least one of $R^5$, $R^6$ and $R^7$ is selected from the group consisting of halogen and lower alkylsulfonylamino.

11. A compound according to claim 1, wherein $R^6$ is halogen or lower alkylsulfonylamino and $R^5$ and $R^7$ are hydrogen.

12. A compound according to claim 1, wherein $R^5$ and $R^6$ are halogen and $R^7$ is hydrogen.

13. A compound according to claim 1 selected from the group consisting of:
- 6-(4-chloro-phenyl)-5-(2,2,2-trifluoro-ethoxy)-3-trifluoromethyl-pyrazine-2-carboxylic acid (2-cyclopropyl-2-hydroxy-propyl)amide,
- 6-(4-chloro-phenyl)-5-cyclopropylmethoxy-3-trifluoromethyl-pyrazine-2-carboxylic acid ((1R,2R)-2-hydroxy-cyclohexyl)-amide,
- 6-(4-chloro-phenyl)-5-cyclopropylmethoxy-3-trifluoromethyl-pyrazine-2-carboxylic acid (2-cyclopropyl-2-hydroxy-propyl)amide,
- 6-(3-chloro-phenyl)-5-(2,2,2-trifluoro-ethoxy)-3-trifluoromethyl-pyrazine-2-carboxylic acid ((1R,2R)-2-hydroxy-cyclohexyl)-amide, and pharmaceutically acceptable salts thereof.

14. A compound according to claim 1 selected from the group consisting of:
- 6-(3-chloro-phenyl)-5-(2,2,2-trifluoro-ethoxy)-3-trifluoromethyl-pyrazine-2-carboxylic acid (2-cyclopropyl-2-hydroxy-propyl)amide,
- 6-(3-chloro-phenyl)-5-cyclopropylmethoxy-3-trifluoromethyl-pyrazine-2-carboxylic acid ((1R,2R)-2-hydroxy-cyclohexyl)-amide,
- 6-(3-chloro-phenyl)-5-cyclopropylmethoxy-3-trifluoromethyl-pyrazine-2-carboxylic acid (2-cyclopropyl-2-hydroxy-propyl)amide,
- 6-(3-chloro-phenyl)-5-phenoxy-3-trifluoromethyl-pyrazine-2-carboxylic acid ((1R,2R)-2-hydroxy-cyclohexyl)-amide, and pharmaceutically acceptable salts thereof.

15. A compound according to claim 1 selected from the group consisting of:
- 6-(3-chloro-phenyl)-5-phenoxy-3-trifluoromethyl-pyrazine-2-carboxylic acid (2-cyclopropyl-2-hydroxy-propyl)-amide,
- 6-(3-chloro-phenyl)-5-(pyridin-2-ylmethoxy)-3-trifluoromethyl-pyrazine-2-carboxylic acid ((1R,2R)-2-hydroxy-cyclohexyl)-amide,
- 6-(3-chloro-phenyl)-5-(pyridin-2-ylmethoxy)-3-trifluoromethyl-pyrazine-2-carboxylic acid (2-cyclopropyl-2-hydroxy-propyl)-amide,
- 6-(3,4-dichloro-phenyl)-5-(2,2,2-trifluoro-ethoxy)-3-trifluoromethyl-pyrazine-2-carboxylic acid ((1R,2R)-2-hydroxy-cyclohexyl)-amide, and pharmaceutically acceptable salts thereof.

16. A compound according to claim 1 selected from the group consisting of:
- 6-(3,4-dichloro-phenyl)-5-(2,2,2-trifluoro-ethoxy)-3-trifluoromethyl-pyrazine-2-carboxylic acid (2-cyclopropyl-2-hydroxy-propyl)-amide,
- 6-(3,4-dichloro-phenyl)-5-cyclopropylmethoxy-3-trifluoromethyl-pyrazine-2-carboxylic acid ((1R,2R)-2-hydroxy-cyclohexyl)-amide,
- 6-(3,4-dichloro-phenyl)-5-cyclopropylmethoxy-3-trifluoromethyl-pyrazine-2-carboxylic acid (2-cyclopropyl-2-hydroxy-propyl)-amide,
- 6-(3,4-dichloro-phenyl)-5-phenoxy-3-trifluoromethyl-pyrazine-2-carboxylic acid ((1R,2R)-2-hydroxy-cyclohexyl)-amide,
- 6-(3,4-dichloro-phenyl)-5-phenoxy-3-trifluoromethyl-pyrazine-2-carboxylic acid (2-cyclopropyl-2-hydroxy-propyl)-amide, and pharmaceutically acceptable salts thereof.

17. A compound according to claim 1 selected from the group consisting of:
- 6-(3,4-dichloro-phenyl)-5-(pyridin-2-ylmethoxy)-3-trifluoromethyl-pyrazine-2-carboxylic acid ((1R,2R)-2-hydroxy-cyclohexyl)-amide,
- 6-(3,4-dichloro-phenyl)-5-(pyridin-2-ylmethoxy)-3-trifluoromethyl-pyrazine-2-carboxylic acid (2-cyclopropyl-2-hydroxy-propyl)-amide,
- 6-(4-methanesulfonylamino-phenyl)-5-(2,2,2-trifluoro-ethoxy)-3-trifluoromethyl-pyrazine-2-carboxylic acid ((1R,2R)-2-hydroxy-cyclohexyl)-amide,
- 6-(4-methanesulfonylamino-phenyl)-5-(2,2,2-trifluoro-ethoxy)-3-trifluoromethyl-pyrazine-2-carboxylic acid (2-cyclopropyl-2-hydroxy-propyl)amide,
- 6-(4-methanesulfonylamino-phenyl)-5-cyclopropylmethoxy-3-trifluoromethyl-pyrazine-2-carboxylic acid ((1R,2R)-2-hydroxy-cyclohexyl)-amide, and pharmaceutically acceptable salts thereof.

18. A compound according to claim 1 selected from the group consisting of:
- 6-(4-methanesulfonylamino-phenyl)-5-cyclopropylmethoxy-3-trifluoromethyl-pyrazine-2-carboxylic acid (2-cyclopropyl-2-hydroxy-propyl)-amide,
- 6-(4-methanesulfonylamino-phenyl)-5-phenoxy-3-trifluoromethyl-pyrazine-2-carboxylic acid ((1R,2R)-2-hydroxy-cyclohexyl)-amide,
- 6-(4-methanesulfonylamino-phenyl)-5-phenoxy-3-trifluoromethyl-pyrazine-2-carboxylic acid (2-cyclopropyl-2-hydroxy-propyl)-amide,
- 6-(4-methanesulfonylamino-phenyl)-5-(pyridin-2-ylmethoxy)-3-trifluoromethyl-pyrazine-2-carboxylic acid ((1R,2R)-2-hydroxy-cyclohexyl)-amide,
- 6-(4-methanesulfonylamino-phenyl)-5-(pyridin-2-ylmethoxy)-3-trifluoromethyl-pyrazine-2-carboxylic acid (2-cyclopropyl-2-hydroxy-propyl)amide, and pharmaceutically acceptable salts thereof.

19. A pharmaceutical composition comprising a therapeutically effective amount of a compound according to claim 1 and a pharmaceutically acceptable carrier.

20. A process for the manufacture of a compound according to claim 1, which process comprises:
coupling a compound of formula II,
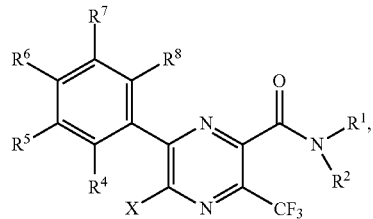
wherein X is halogen and $R^1$, $R^2$ and $R^4$ to $R^8$ are as defined in claim 1, with an alcohol of formula III,
$$R^3\text{—OH} \qquad \qquad \text{III,}$$
wherein $R^3$ is as defined as in claim 1, in the presence of a suitable base.
* * * * *